United States Patent [19]

Björck

[11] 4,320,116

[45] Mar. 16, 1982

[54] FOODSTUFFS, ANIMAL FEEDING STUFFS AND PHARMACEUTICAL PREPARATIONS CONTAINING AN ANTIBACTERIAL SYSTEM

[75] Inventor: Karl E. L. Björck, Upsala, Sweden

[73] Assignee: Astra-Ewos AB, Sodertalje, Sweden

[21] Appl. No.: 75,245

[22] Filed: Sep. 13, 1979

Related U.S. Application Data

[63] Continuation of Ser. No. 774,649, Mar. 4, 1977, abandoned.

[30] Foreign Application Priority Data

Mar. 8, 1976 [SE] Sweden ............................ 7603075

[51] Int. Cl.$^3$ .................... A61K 31/17; A61K 33/00; A61K 33/40
[52] U.S. Cl. ................................ 424/129; 424/130; 424/322
[58] Field of Search ...................... 424/129, 130, 322

[56] References Cited

PUBLICATIONS

Klebanoff et al., Biochem et Biophysica Acta 117(1), 63–72, (1966).
Gothefors et al., Infection and Immunity, 6/75, vol. 11, No. 6, pp. 1210–1215.
Bjorck et al., Applied Microbiology, Aug. 1975, pp. 199–204.

*Primary Examiner*—Allen J. Robinson
*Attorney, Agent, or Firm*—Brumbaugh, Graves, Donohue & Raymond

[57] ABSTRACT

Process for preparing foodstuffs and animal feeding stuffs containing an antibacterial system, as well as such foodstuffs and animal feeding stuffs, and method for more efficient meat production using such feeding stuffs, an antibacterial system and a method for treating bacterial infections in mammals including humans and a pharmaceutical preparation containing an antibacterial system, whereby the antibacterial system comprises a thiocyanate, a solid, water-soluble peroxide donor and lactoperoxidase.

13 Claims, No Drawings

FOODSTUFFS, ANIMAL FEEDING STUFFS AND PHARMACEUTICAL PREPARATIONS CONTAINING AN ANTIBACTERIAL SYSTEM

This is a continuation of application Ser. No. 774,649 filed Mar. 4, 1977 now abandoned.

The present invention relates to a process for preparing new foodstuffs and animal feedstuffs comprising an antibacterial system, such foodstuffs and animal feedstuffs, a process for increasing meat production, pharmaceutical preparations containing the same, and an antibacterial system.

One object of the present invention is to obtain foodstuffs and animal feedstuffs comprising an antibacterial system, which system exerts an antibacterial effect in the gastrointestinal tract.

It is previously known that domestic animal live stocks, especially young animals, are subjected to severe gastrointestinal infections which mainly depend on infections of *E.coli* and different species of Salmonella. Hitherto known methods to eliminate these infections include thereby either the administration of a therapeutical amount of antibiotics with the risk for the formation of antibiotic resistent bacterial species attached thereto, or to carry out a vaccination of the live stocks, which leads to high costs as vaccines and vaccinations are relatively expensive. An other chemotherapeutically active agent used is i.a. trimethoprimsulpha.

It has now surprisingly been found possible to avoid these drawbacks last mentioned, and to prevent and/or eliminate such bacterial infections by means of the present invention, which is characterized in that an antibacterial system containing lactoperoxidase, thiocyanate and a solid, watersoluble peroxide donor selected from the group alkalipercarbonates, earth alkali peroxides, and carbamide peroxide is added to foodstuff and animal feedstuff compositions known per se.

According to a preferred embodiment the invention is characterized in that thiocyanate is added in an amount of at least 16 ppm of the foodstuff calculated as NaSCN, a solid watersoluble peroxide donor is added in an amount of at least 21 ppm of the foodstuff calculated as Na-percarbonate, and lactoperoxidase is added in an amount of at least 1 mg/kg foodstuff, whereby lactoperoxidase is added in purified form and/or in the form of a lactoperoxidase-containing milk product, and whereby the molar relationship between peroxide donor and thiocyanate is less than 4, preferably 1-2.

According to a preferred embodiment thiocyanate is added in an amount of 160-3500, preferably 160-1750 ppm foodstuff calculated as NaSCN, the peroxide donor in an amount of 210-4000, preferably 210-2000, ppm foodstuff calculated as Na-percarbonate, and lactoperoxidase in an amount of 10-200, preferably 10-100, mg.

The amounts given above of the active ingredients are given so thiocyanate is added in such an amount that the concentration thereof in the digestive tract is at least 0.1 mM, a solid watersoluble peroxide donor in such an amount that the concentration thereof in the digestive tract expressed as $H_2O_2$ is at least 0.1 mM and lactoperoxidase in purified form and/or in the form of a lactoperoxidase-containing milk product in such an amount that the concentration thereof in the digestive tract is at least 1 mg/l.

The watersoluble peroxide donor consists preferably of sodium percarbonate, which has been coated with a protecting layer, which is soluble in the intestinal tract, and which layer preferably consists of cellulose acetatephtalate.

According to another aspect of the invention this comprises new foodstuffs and animal feedstuffs, which are characterized in that the antibacterial system comprises lactoperoxidase, thiocyanate, and a solid, watersoluble peroxide donor from the group alkalipercarbonates, earth alkali peroxides and carbamide peroxide.

According to a further aspect of the invention this comprises a process for more efficient meat production, whereby calves and pigs are administered nutritional elements known per se and an antibacterial system, whereby the invention is characterized in that one adds an antibacterial system comprising lactoperoxidase, a thiocyanate, and a solid, watersoluble peroxide donor from the group alkalipercarbonates, earth alkali peroxides, and carbamide peroxide, whereby thiocyanate is added in such an amount that the concentration thereof in the digestive tract is at least 0.1 mM, a peroxide donor is added in such an amount calculated as $H_2O_2$ that the concentration thereof in the digestive tract is at least 0.1 mM, and lactoperoxidase is added in such an amount that the concentration thereof in the digestive tract is at least 1 mg/l.

According to still a further aspect of the invention this comprises an antibacterial system which is characterized in that it comprises lactoperoxidase, a thiocyanate, and a solid, watersoluble peroxide donor from the group alkalipercarbonates, earth alkali peroxides and carbamide peroxide.

A further aspect of the invention is a method for treating gastrointestinal infections in mammals, including man, suffering from gastrointestinal infections caused by bacterias, whereby a therapeutically effective amount of the antibacterial system given above is administered orally.

Another aspect of the invention is pharmaceutical preparations comprising the antibacterial system given above together with a pharmaceutically acceptable carrier.

Animals treated are normally pigs, calves, and poultry, and furproducing animals as minks and foxes. Pets as cats and dogs may also be treated.

The amount of thiocyanate is selected in such a way that one obtains a concentration thereof of at least 0.1, preferably 0.2-0.4 mM, whereby concentrations of 0.5-1.0 mM may be useful in certain cases, in the digestive tract, whereby the concentration should not exceed toxical concentrations (10 mM). The amount of peroxide donor is selected in such a way that an equimolar amount of $H_2O_2$ is obtained, i.e. that the concentration of $H_2O_2$ formed exceeds to at least 0.1 preferably 0.2-0.4 mM. The concentration of $H_2O_2$ shall in each case be less than 4 times the concentration of thiocyanate. The amount of lactoperoxidase is dependent on the activity of the enzyme but based on the assumption that 1 mg contains 50 units (U), at least 1 mg of enzyme should be present per liter of digestive juice.

In a solution the concentration of thiocyanate is thus at least 0.1 mM, preferably 0.2-0.4 mM, the concentration of peroxide donor such that the concentration of $H_2O_2$ is 0.1 mM, preferably 0.2-0.4 mM, and the concentration of lactoperoxidase is 1 mg/l (50 U/l). The latter may be varied, too, but should be 1-2 mg/l (50-100 U/l).

1 unit of lactoperoxidase is the amount of lactoperoxidase which forms 1 mg of purogalline from purogallol in 20 sec. at pH 6.0 and 20° C.

The amount of lactoperoxidase in bovine whey (unpasteurized) or in ultrafiltrated whey may of course vary. Bovine milk contains, according to the literature, lactoperoxidase in an amount of about 30 mg/l, whereby the amount of lactoperoxidase in human milk, according to the literature, is about 1/30 of that in bovine milk. Lactoperoxidase is also found in other bovine milk products as skim milk powder, which may be used as well.

Salts of thiocyanate used are the sodium, potassium, and ammonium salts.

$LD_{50}$ of thiocyanate is 484 mg/kg bodyweight when injected intravenously in mice and is 764 mg/kg bodyweight when administered orally to rat.

In clinical use the compounds of the invention are administered normally orally, as rectally in the form of a pharmaceutical preparation, which contains an antibacterial system according to the invention in combination with a pharmaceutical carrier.

Thereby the mentioning of the new antibacterial system of the invention is here related to any peroxide donor and/or any thiocyanate, even if the compounds are generally or specifically described, provided that the context in which such expressions are used, e.g. in the examples, with this broad meaning should not correspond. The carrier may be a solid, semisolid or liquid diluent or a capsule. These pharmaceutical preparations are a further object of the invention. Usually the amount of active ingredients is between 0.1 to 99% by weight of the preparation, suitably between 2 to 50% by weight in preparations for oral administration.

In the preparation of pharmaceutical preparations containing an antibacterial system of the present invention in the form of dosage units for oral administration the ingredients elected may be mixed with a solid, pulverulent carrier, as e.g. with lactose, saccharose, sorbitol, mannitol, starch, as potatoe starch, corn starch, amylopectin, cellulose derivatives or gelatine, as well as with an antifriction agent as magnesium stearate, calcium stearate, polyethylene-glycol waxes or the like, and be pressed into tablets. If coated tablets are wanted, the above prepared core may be coated with a solution of a polymer which dissolves or is permeable in the intestinal tract. To this coating a dye may be added in order to easily distinguish between tablets with different active compounds or with different amount of the active compound present.

In the preparation of soft gelatine capsules (pearl-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier as lactose, saccharose, sorbitol, mannitol, starch (as e.g. potatoe starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of sirups or suspensions, e.g. solutions containing from about 0.2% by weight to about 20% by weight of the active substances described, whereby the residue consists of sugar and a mixture of ethanol, water, glycerol and propylene glycol. If desired, such liquid preparations may contain colouring agents, flavouring agents, saccharine and carboxymethylcellulose as a thickening agent. The peroxide donor is thereby present in form of microencapsulated particles.

The preparation of pharmaceutically tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed during a continuous and constantly mixing with the binding agent solution which may consist of a polymer which dissolves or is permeable in the intestinal juices and are moistened so that the solution is uniformly divided in the mass without overmoistening any parts. The amount of solvent is usually so adapted that the mass obtains a consistency reminding of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the damp degree of the granulate is of utmost importance for the following process and for the feature of the tablets. Drying in a fluid bed may possibly be used. In this case the mass is not put on a tray but is poured into a container having a net bottom.

After the drying step the granules are sieved so that the particle size wanted is obtained. Under certain circumstances powder has to be removed.

To the so called final mixture, disintegrating, antifriction agents and antiadhesive agents are added. After this mixture the mass shall have its right composition for the tabletting step.

The cleaned tablet punching machine is provided with a certain set of punches and dies, whereupon the suitable adjustment for the weight of the tablets and the degree of compression is tested out. The weight of the tablet is decisive for the size of the dose in each tablet and is calculated starting from the amount of therapeutic agent in the granules. The degree of compression affects the size of the tablet, its strength and its ability of disintegrate in water. Especially as regards the two later properties the choice of compression pressure (0.5 to 5 ton) means something of a balance-step. When the right adjustment is set, the preparation of tablets is started which is carried out with a rate of 20,000 to 200,000 tablets per hour. The pressing of the tablets requires different times and depends on the size of the batch.

The tablets are preferably coated with a coating. This means that these are coated with a layer of a polymer dissolvable or permeable in the intestinal tract.

The tablets are usually packed by machines having an electronic counting device. The different types of packages consist of glass or plastic gallipots but also boxes, tubes and specific dosage adapted packages.

The daily dose of the active substance varies and is depending on the type of administration and bacterial infection, but as a general rule it is 8 to 400 mg/day of Na-thiocyanate and 10 to 500 mg/day of Na-percarbonate at peroral administration.

Pharmaceutical preparations containing an antibacterial system according to the invention are intended to be used in the treatment of bacterial infections in the gastrointestinal tract caused e.g. by Shigella, Salmonella, E.coli, Vibreo colera, Pseudomonas (Ps. pyocyanea), Staphylococcus (Staph. albus, aureus), Streptococcus (Strep. viridans, Strep. faecalis, β-Streptococcus), Proteus.

The present invention will be described more in detail in the following with reference to the Examples below, however, without being limited thereto.

EXAMPLE 1

A milk replacer was prepared from the following ingredients:

| | |
|---|---|
| 2 kg | of ultrafiltrated wheypowder (500 mg of lactoperoxidase/kg) |
| 56 kg | of wheypowder |
| 8 kg | of fat |
| 20 kg | of animal protein |
| 4 kg | of vitamins, minerals |
| 100 kg | |
| | and |
| 21 g | of sodium percarbonate |
| 16 g | of sodium thiocyanate. |

The ingredients were thoroughly mixed in a mixer. At the use thereof water is added to the dry mixture until a 10% aqueous solution is obtained (10% dry mixture). Such a milk replacer solution is normally administered in an amount of 4 liters per day and calf. (=400 g of dry product per day).

The amount of sodium percarbonate may be varied in such a milk replacer between 210–420 ppm and the amount of thiocyanate between 160–320 ppm, whereby Na-percarbonate:NaSCN=21:16.

EXAMPLE 2

A feedstuff of addition for piglets was prepared from the following ingredients:

| | |
|---|---|
| 66.0 kg | of feedstuff flour (steamtreated oats) |
| 10.0 kg | of iron salts ($Fe^{2+}$ - salts) |
| 3.5 kg | of vitamins (vit. A, D, E, and C) |
| 0.5 kg | of trace elements (Cu, Co, I, Mn, Zn) |
| 20.0 kg | of ultrafiltrated wheypowder (500 mg of LP/kg) |
| 100.0 kg | |
| | and |
| 210 g | of sodium percarbonate |
| 160 g | of sodium thiocyanate |

The ingredients were thoroughly mixed in a mixer. The feedstuff is administered in dry form directly on the floor to the pigs from the age of 2 days to the age of 28 days. The daily dose of such a feedstuff is about 5 g per piglet, whereby the amount at each feeding occasion is about 0.5 g/piglet. The amount of sodium percarbonate may be varied in such a feedstuff between 2100–4200 ppm and the amount of sodium thiocyanate between 1600–3200 ppm, whereby the relation Na-percarbonate:NaSCN=21:16.

EXAMPLE 3

A feedstuff for piglets was prepared from the following ingredients. The feedstuff is intended to be used when no sow milk is at hand or when very early weaning is considered.

| | |
|---|---|
| 60.0 kg | of skim milk powder |
| 3.5 kg | of ultrafiltrated whey powder (500 mg of LP/kg) |
| 15.0 kg | of corn (ground, steamtreated oats and/or barley) |
| 5.0 kg | of fat |
| 3.0 kg | of hydrolyzed corn starch |
| 2.5 kg | of raw sugar |
| 6.0 kg | of glucose |
| 5.0 kg | of vitamins and minerals |
| 100.0 kg | |
| | and |
| 35 g | of sodium percarbonate |
| 27 g | of sodium thiocyanate |

The ingredients were thoroughly mixed in a mixer. The feedstuff is administered in dry form to the pigs whereby the feedstuff is given ad libitum. The daily intake is about 30–50 g depending on the age of the piglet.

The amount of sodium percarbonate may hereby be varied between 350–700 ppm, and the amount of NaSCN between 270–540 ppm Na-percarbonate:-NaSCN being 21:16.

EXAMPLE 4

A vitaminized mineral feedstuff for swine, as mother-sows, was prepared from the following ingredients.

| | |
|---|---|
| 33.0 kg | of calcium salt |
| 35.0 kg | of calcium/phosphorus salt ($CaHPO_4 \cdot 2H_2O$) |
| 13.0 kg | of sodium chloride |
| 0.4 kg | of B-vitamin mixture |
| 0.4 kg | of vitamins A, C, D, and E |
| 1.2 kg | of trace element mixture (Fe, Zn, Mn, Cu, I) |
| 17.0 kg | of ultrafiltrated whey powder (500 mg of LP/kg) |
| 100.0 kg | |
| | and |
| 174 g | of sodium percarbonate |
| 135 g | of sodium thiocyanate |

The ingredients of the mineral feedstuff were thoroughly mixed and are diluted with corn and protein sources known and used per se. 3% of the vitaminized mineral feedstuff are used in the end mixture. Alternatively the vitaminized mineral feedstuff may be administered in amounts of about 30–150 g per animal and day directly into the trough without incorporation. The amount of sodium percarbonate may hereby be varied between 1740–3480 ppm, and the amount of NaSCN between 1350–2700 ppm, Na-percarbonate:NaSCN being 21:16.

EXAMPLE 5

An electrolyte mixture was prepared from the following ingredients:

| | |
|---|---|
| 1.0 kg | of potassium chloride |
| 20.0 kg | of sodium chloride |
| 15.0 kg | of sodium bicarbonate |
| 64.0 kg | glucose |
| 100.0 kg | |
| | and |
| 97 g | of sodium percarbonate |
| 75 g | of sodium thiocyanate |
| 5 g | of lactoperoxidase (50 U/mg) |

The electrolyte mixture thoroughly mixed is used as follows: 25 g thereof is dissolved in 1 liter of water and is administered to pig or calf in an amount of about 10% of the bodyweight daily at established dehydration, or in order to prevent dehydration.

The amount of sodium percarbonate may be varied between 970–1940 ppm, and the amount of sodium thiocyanate between 750–1500 ppm, the amount of Na-percarbonate:the amount of NaSCN being 21:16.

EXAMPLE 6

A gruel intended for small children was prepared from the following ingredients

| | |
|---|---|
| 50.5 kg | of desalinated wheypowder |
| 19.0 kg | of skim milk powder ($\geq$ 100 mg LP/kg) |
| 14.0 kg | of fat mixture |
| 8.0 kg | of lactose |
| 7.5 kg | of steamtreated rice flour |
| 1.0 kg | of vitamins and minerals |
| 100.0 kg | |
| | and |
| 21 g | sodium percarbonate |
| 16 g | sodium thiocyanate |

The ingredients were thoroughly mixed in a mixer. The dry gruel mixture is dissolved in water having a temperature of about 30°–35° C. as a 10–15% aqueous solution (10–15% dry matter) and is given in an amount of about 0.2 liters 4–5 times a day.

The amount of sodium percarbonate may be varied in such a gruel between 210–420 ppm and the amount of sodium thiocyanate between 160–320, whereby the amounts are preferably equimolar.

The sodium percarbonate used in Examples 1–6 above has been protected against too early reaction by coating a granulate thereof with a layer of a polymer which dissolves or is permeable in the intestinal tract at first.

Such protecting polymers are waxes, cellulose acetate phtalate, and similar polymers which dissolve or are permeable in the intestinal tract. Further, a double coating may be used if a suspension before administration should give an alkaline environment.

Pharmaceutical preparations were prepared in accordance with the following examples.

EXAMPLE 7

| | |
|---|---|
| Sodiumpercarbonate granules containing 10% of active oxygen | 100 g |
| Sodium thiocyanate | 40 g |
| Lactoperoxidase (50 U/mg) | 2 g |
| Polyvinylpyrrolidone | 10 g |
| Lactose | 50 g |
| Magnesiumstearate | 10 g |

The lactoperoxidase was mixed with lactose and was granulated using a solution of polyvinylpyrrolidone.

Sodium percarbonate was mixed with sodium thiocyanate and the lactoperoxidase granules. Magnesium stearate was added, whereupon the granular mixture was tabletted.

The tablets obtained having an average weight of 212 mg was coated with a gastric juice resistant layer consisting of Eudragit ®.

EXAMPLE 8

| | | |
|---|---|---|
| Magnesium peroxide | 50 | g |
| Sodium thiocyanate | 0.8 | g |

-continued

| | | |
|---|---|---|
| Lactoperoxidase (50 U/mg) | 0.04 | g |
| Polyvinylpyrrolidone | 5 | g |
| Lactose | 100 | g |
| Magnesium stearate | 2 | g |

The three active components are each granulated per se using polyvinylpyrrolidone as granulating agent. Lactose and magnesium-stearate are added, whereupon the mixture is tabletted. The tablets obtained (1000 pieces) having an average weight of about 155 mg are coated with a solution of cellulose acetatephtalate being resistent to gastric juice, in a solvent mixture of acetone and isopropanol (equal parts).

EXAMPLE 9

| | |
|---|---|
| Carbamide peroxide | 50 g |
| Sodium thiocyanate | 20 g |
| Lactoperoxidase (50 U/mg) | 1 g |
| Lactose | 100 g |
| Stearic acid powder | 2 g |

The carbamide peroxide is granulated using a solution of Eudragit ® S. The lactoperoxidase is mixed with lactose and thiocyanate, and the mixture is granulated using Eudragit ® S. The two batches of granules are combined and mixed with stearic acid powder and the final mixture is tabletted. The tablets have an average weight of about 175 mg.

EXAMPLE 10

| | | |
|---|---|---|
| I | Sodium percarbonate | 100 g |
| | Mannitol | 20 g |
| II | Sodium thiocyanate | 40 g |
| | Mannitol | 20 g |
| III | Lactoperoxidase | 2 g |
| | Mannitol | 20 g |

Granulates were prepared from each of I, II, and III using a solution of Eudragit ® L. The granules combined were mixed with a suitable flavoring agent as sugar, cocoa, microencapsulated citrus aroma, or mixtures thereof.

A dosage device, e.g a spoon, which provides for a dose of about 200 mg is enclosed with the package of the granular mixture. The package is made of a moist-tight material as e.g. a laminated aluminium foil.

Biological effect 4 test tubes containing 10 mls of whey having a content of 21 ppm (0.25 mM) of NaSCN were incubated at 30° C., the whey having been inoculated with $Ps.$ $fluorescens$ EF 1998. One tube was control. Sodium percarbonate corresponding to 0.1 mM, 0.2 mM, and 0.3 mM, respectively, of $H_2O_2$ was added to the respective three other tubes. The amount of bacterias was determined at inoculation and after 2 hrs of incubation. Lactoperoxidase is present in 5 µg/ml. The result is given in Table 1 below.

TABLE 1

| Na-percarbonate corresponding to | Number of bacterias/ml | |
|---|---|---|
| mM $H_2O_2$ | 0 hr | 2 hrs |
| Control (0.0 mM) | $2.1 \cdot 10^6$ | $2.1 \cdot 10^6$ |
| 0.1 mM | $2.1 \cdot 10^6$ | $1.8 \cdot 10^5$ |

TABLE 1-continued

| Na-percarbonate corresponding to mM $H_2O_2$ | Number of bacterias/ml | |
|---|---|---|
| | 0 hr | 2 hrs |
| 0.2 mM | $2.1 \cdot 10^6$ | $2.8 \cdot 10^3$ |
| 0.3 mM | $2.1 \cdot 10^6$ | $2.6 \cdot 10^3$ |

As evident therefrom a striking improvement of the antibacterial effect is obtained when 0.2 mM $H_2O_2$ or more are present. Already the addition of 0.1 mM $H_2O_2$ gives, however, a striking bactericidal effect.

Ps. fluorescens EF 1998 was incubated at +30° C. in two tubes (1) and (2), whereby tube (1) contained 1 g of a commercial milk replacer comprising 15% of ultrafiltrated whey powder, 57% of whey powder, 8% of fat, 16% of animalic protein, and 4% of vitamins, and minerals in 10 mls of water, whereby it contained 50 μg of lactoperoxidase and 27.5 ppm of sodium percarbonate were added thereto, and whereby tube (2) contained the same amount of milk replacer (50 μg of lactoperoxidase) and whereby 21 ppm of sodium thiocyanate and 27.5 ppm of sodium percarbonate were added.

The amount of bacterias in the different tubes is given in Table 2 below, where the result after 0, 2, 4 and 6 hrs is given.

TABLE 2

| Sample | 0 | 2 | 4 | 6 hrs |
|---|---|---|---|---|
| Tube 1 | $4.5 \cdot 10^6$ | $3.5 \cdot 10^6$ | $5.3 \cdot 10^6$ | $6.0 \cdot 10^6$ |
| Tube 2 | $4.5 \cdot 10^6$ | $3.5 \cdot 10^5$ | $5.3 \cdot 10^4$ | $5.6 \cdot 10^3$ |

As evident from the table the amount of bacterias in tube (2) after 6 hrs is only 1/1000 of the amount in tube (1) at the same time, whereby no or only slight growth has taken place in tube (1) but instead a killing has taken place in tube (2).

The effect of the antibacterial system was determined in vitro. Thereby different E.coli strains were incubated at +37° C. in an aqueous solution of 5 g of whey-powder/100 ml, 21 ppm of NaSCN and sodium percarbonate corresponding to 0.25 mM $H_2O_2$. The result of the E.coli-killing after 2 hrs is given in Table 3 below.

TABLE 3

| E. coli strain | | % killed |
|---|---|---|
| 0-139 | 299/66 | >99.98 |
| 0-149 | 853/67 | >99.98 |
| 0-138 | 355/67 | >99.95 |
| 0-8 | 915/66 | >99.99 |
| 0-147 | 949/66 | >99.99 |
| 0-141 | 220/65 | >99.99 |

Several of the E.coli strains tested above are resistent to antibiotics. Thus the results indicate a high degree of application of the system.

A high degree of application is also present as the system has an effect on gram positive bacterias, too.

The antibacterial system according to the invention may also be utilized in foodstuffs for human use as well as in pharmaceutical preparations for veterinarian and human use. As pharmaceutical preparations solid as well as liquid preparations may be used, whereby the antibacterial system is generally added to pharmaceutical carriers of different kinds, depending on type and amount used.

A milk replacer intended for calves and containing 45% by weight of skim milk powder (≧40 mg LP/kg), 22.5% by weight of whey powder, 12.5% by weight of soya meal, 15.0% by weight of animal fat, 4.5% by weight of lactalbumins and 0.5% by weight of vitamins was used in a test against E.coli 9703. The strain was incubated at +37° C. in a 10% aqueous solution of the milk replacer containing 5 μg/ml of lactoperoxidase. Two different concentrations of NaSCN and three different concentrations of $H_2O_2$ in form of Na-percarbonate were used, as given in Table 4 below.

TABLE 4

| Conc. in mM | | Number of bacterias/ml | |
|---|---|---|---|
| $SCN^-$ | $H_2O_2$ | at 0 hrs | 2 hrs |
| 0.25 | 0 | $2.5 \cdot 10^6$ | $7.7 \cdot 10^7$ |
| 0.25 | 0.25 | $2.5 \cdot 10^6$ | $5.3 \cdot 10^4$ |
| 0.50 | 0 | $1.8 \cdot 10^6$ | $1.0 \cdot 10^8$ |
| 0.50 | 0.50 | $1.8 \cdot 10^6$ | $1.5 \cdot 10^4$ |

As evident from Table 4 the antibacterial system gives a strong bactericidal effect in both concentrations tested, simultaneously as it is shown that $SCN^-$ has no effect per se, but bacterial growth continues when no peroxide donor is present.

I claim:

1. Foodstuff and animal feedstuff comprising foodstuff and animal agents as an antibacterial system capable of being activated in the gastrointestinal tract, the antibacterial system comprising lactoperoxidase, a thiocyanate selected from the group consisting of sodium thiocyanate, potassium thiocyanate and ammonium thiocyanate and a solid water soluble peroxide donor selected from the group consisting of an alkali percarbonate, an alkali earth metal peroxide and a carbamide peroxide, wherein the thiocyanate is present in an effective amount of at least 16 ppm of the total composition calculated as NaSCN, the solid, water soluble peroxide donor is present in an effective amount of at least 21 ppm of the total composition calculated as sodium percarbonate, and lactoperoxidase is present in the form of a lactoperoxidase-containing milk product in an effective amount of at least 1 mg/kg of the total composition, the molar relationship between peroxide donor and thiocyanate being less than 1–2:1.

2. Foodstuff and animal feedstuff according to claim 1 wherein the sodium percarbonate is provided with a protective layer selected from the group consisting of waxes and polymers which dissolves and becomes permeable in the intestinal tract.

3. Foodstuff and animal feedstuff according to claim 1, wherein the thiocyanate is present in an effective amount of at least 16 ppm of the total composition calculated as NaSCN, the solid, water soluble peroxide donor is present in an effective amount of at least 21 ppm of the total composition calculated as sodium percarbonate, and the lactoperoxidase is in pure form in an effective amount of at least 1 mg/kg of the total composition, the molar relationship between peroxide donor and thiocyanate being less than 1–2:1.

4. Foodstuff and animal feeding stuff according to claim 1, wherein the thiocyanate is present in an amount of 160–3500 ppm calculated as sodium thiocyanate, the peroxide donor is present in an amount of 210–4000 ppm calculated as sodium percarbonate, and lactoperoxidase is present in an amount of 10–200 mg/kg.

5. Foodstuff and animal feeding stuff according to claim 3, wherein the thiocyanate is present in an amount of 160–3500 ppm calculated as sodium thiocyanate, the peroxide donor is present in an amount of 210–4000 ppm calculated as sodium percarbonate, and lactoperoxidase is present in an amount of 10-200 mg/kg.

6. Foodstuff and animal feeding stuff according to claim 1 or 3, wherein the thiocyanate is present in an amount of 160-1750 ppm calculated as sodium thiocyanate, the peroxide donor is present in an amount of 210-2000 ppm calculated as sodium percarbonate, and lactoperoxidase is present in an amount of 10-100 mg/kg.

7. A method for more efficient meat production comprising feeding to meat producing animals a feeding stuff containing an amount of an antibacterial system effective to increase meat production, the system comprising lactoperoxidase, a thiocyanate selected from the group consisting of sodium thiocyanate, potassium thiocyanate and ammonium thiocyanate and a solid, water soluble peroxide donor selected from the group consisting of an alkali metal percarbonate, an alkali earth metal peroxide, and carbamide peroxide, wherein the thiocyanate calculated as NaSCN being administered in an effective amount of at least 16 ppm of the feeding stuff and sufficient that the thiocyanate concentration in the intestinal tract is at least 0.1 mM, the peroxide donor calculated as sodium percarbonate being administered in an effective amount of at least 21 ppm of the feeding stuff and sufficient that the concentration calculated as $H_2O_2$ in the intestinal tract is at least 0.1 mM, and the lactoperoxidase being administered in an effective amount of at least 1 mg/kg of the feeding stuff, and sufficient that the lactoperoxidase concentration in the intestinal tract is at least 1 mg/l of intestinal contents, the molar relationship between the peroxide donor and the thiocyanate being less than 4:1.

8. A method according to claim 7, wherein the thiocyanate is administered in an effective amount of at least 16 ppm of the feeding stuff calculated as NaSCN in such an amount that the concentration thereof in the intestional tract is at least 0.1 mM, the peroxide donor is administered in an effective amount of at least 21 ppm of the feeding stuff calculated as sodium percarbonate in such an amount, calculated as $H_2O_2$, that the concentration thereof in the intestinal tract is at least 0.1 mM, and lactoperoxidase is administered in an effective amount of at least 1 mg/kg of feeding stuff in such an amount that the concentration thereof is at least 1 mg/l of intestinal contents, the molar relationship between the peroxide donor and thiocyanate being less than 1-2:1.

9. A method according to claim 7, wherein the thiocyanate is present in an amount of 160-3500 ppm calculated as sodium thiocyanate, the peroxide donor is present in an amount of 210-4000 ppm calculated as sodium percarbonate, and lactoperoxidase is present in an amount of 10-200 mg/kg.

10. A method according to claim 8, wherein the thiocyanate is present in an amount of 160-3500 ppm calculated as sodium thiocyanate, the peroxide donor is present in an amount of 210-4000 ppm calculated as sodium percarbonate, and lactoperoxidase is present in an amount of 10-200 mg/kg.

11. A method according to claim 7, wherein the solid, water soluble peroxide donor is administered in the form of sodium percarbonate, which has been provided with a protective layer selected from the group consisting of waxes and polymers which dissolves and becomes permeable in the intestinal tract.

12. A method according to claim 8, wherein the solid, water soluble peroxide donor is administered in the form of sodium percarbonate, which has been provided with a protective layer selected from the group consisting of waxes, and polymers which dissolves and becomes permeable in the intestinal tract.

13. A method according to claim 7, wherein the solid, water soluble peroxide donor is administered in the form of magnesium peroxide, which has been provided with a protective layer selected from the group consisting of waxes and polymers which dissolves and becomes permeable in the intestinal tract.

* * * * *

UNITED STATES PATENT AND TRADEMARK OFFICE
CERTIFICATE OF CORRECTION

PATENT NO. : 4,320,116
DATED : March 16, 1982
INVENTOR(S) : Karl Erik Lennart Björck It is certified that error appears in the above—identified patent and that said Letters Patent is hereby corrected as shown below:

Column 5, Line 22, "56 kg." should read --66 kg.--.

Signed and Sealed this

First Day of June 1982

[SEAL]

Attest:

GERALD J. MOSSINGHOFF

*Attesting Officer*   *Commissioner of Patents and Trademarks*